(12) United States Patent
Lantz et al.

(10) Patent No.: US 11,804,292 B2
(45) Date of Patent: *Oct. 31, 2023

(54) DEVICE FOR STIMULATING TRACHEOBRONCHIAL AIR (71) Applicant: PHYSIO-ASSIST, Aix-en-Provence (FR)

(72) Inventors: Jean-Sebastien Lantz, Aix en Provence (FR); Adrien Mithalal, Montpellier (FR)

(73) Assignee: PHYSIO-ASSIST, Aix-en-Provence (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/649,463

(22) Filed: Jan. 31, 2022

(65) Prior Publication Data

US 2022/0157429 A1 May 19, 2022

Related U.S. Application Data (63) Continuation of application No. 15/743,291, filed as application No. PCT/EP2016/066453 on Jul. 11, 2016, now Pat. No. 11,270,787.

(30) Foreign Application Priority Data

Jul. 10, 2015 (FR) ...................... 1556616

(51) Int. Cl.
*G16H 20/40* (2018.01)
*A61M 16/00* (2006.01)
(Continued)

(52) U.S. Cl.
CPC ........ *G16H 20/40* (2018.01); *A61M 16/0003* (2014.02); *A61M 16/0006* (2014.02);
(Continued)

(58) Field of Classification Search
CPC .............. A61M 16/024; A61M 16/026; A61M 16/022; A61M 16/0003; A61M 16/0006;
(Continued)

(56) References Cited

U.S. PATENT DOCUMENTS 2,918,917 A 12/1959 Emerson
4,710,165 A 12/1987 McNeil et al.
(Continued)

FOREIGN PATENT DOCUMENTS

EP 2 854 918 B1 5/2018
FR 2 733 917 A1 11/1996
(Continued)

OTHER PUBLICATIONS

International Search Report, dated Oct. 7, 2016, from corresponding PCT/EP2016/066453 application.

*Primary Examiner* — Joseph D. Boecker
*Assistant Examiner* — Brian T Khong
(74) *Attorney, Agent, or Firm* — NIXON & VANDERHYE (57) ABSTRACT

Disclosed is a device for stimulating the tracheobronchial air of a patient suffering from an obstructive ventilatory disorder and able to modify the rheology of his tracheobronchial mucus, which includes a negative pressure generator, a physiological interface able to interface the device with the patient's respiratory apparatus, a connection pipe connecting the physiological interface to the negative pressure generator, and a control circuit capable of controlling the negative pressure generator, during the passive expiration phase, for the application of a succession of alternation of negative pressure and venting impulses with a determined frequency and a duty cycle determined during a first part of an expiration cycle and then a second frequency and a second (Continued)

duty cycle during a second part of the expiration cycle and to reiterate a defined number of expiration cycles.

19 Claims, 4 Drawing Sheets

(51) Int. Cl.
  *G16H 40/63* (2018.01)
  *A61M 16/20* (2006.01)
  *G16H 40/60* (2018.01)
(52) U.S. Cl.
  CPC .... *A61M 16/0009* (2014.02); *A61M 16/0051* (2013.01); *A61M 16/024* (2017.08); *A61M 16/202* (2014.02); *G16H 40/63* (2018.01); *A61M 2016/0027* (2013.01); *A61M 2205/505* (2013.01); *A61M 2205/6054* (2013.01); *G16H 40/60* (2018.01)
(58) Field of Classification Search
  CPC .......... A61M 16/0009; A61M 16/0051; A61M 16/202; A61M 16/203; A61M 16/205; A61M 16/204; A61M 2205/505; A61M 2205/502; A61M 1/0031; A61M 1/0037; A61M 1/0023
  See application file for complete search history.

(56) References Cited

U.S. PATENT DOCUMENTS

| | | | | |
|---|---|---|---|---|
| 6,176,235 B1 * | 1/2001 | Benarrouch | .......... | A61M 16/20 128/205.12 |
| 6,581,596 B1 | 6/2003 | Truitt et al. | | |
| 6,968,842 B1 | 11/2005 | Truschel et al. | | |
| 8,028,695 B2 * | 10/2011 | Acker | ............... | A61M 16/0627 128/203.14 |
| 2002/0023644 A1 | 2/2002 | Berthon-Jones | | |
| 2002/0195105 A1 * | 12/2002 | Blue | .................... | A61M 16/024 128/205.25 |
| 2005/0051174 A1 | 3/2005 | Emerson | | |
| 2006/0178592 A1 * | 8/2006 | Nason | .................... | A61B 5/082 600/532 |
| 2007/0157931 A1 * | 7/2007 | Parker | .................. | A61M 11/005 128/204.23 |
| 2007/0169776 A1 | 7/2007 | Kepler et al. | | |
| 2008/0121231 A1 | 5/2008 | Sinderby et al. | | |
| 2009/0126734 A1 | 5/2009 | Dunsmore et al. | | |
| 2010/0180897 A1 | 7/2010 | Malgouyres | | |
| 2011/0220107 A1 | 9/2011 | Kimm et al. | | |
| 2012/0136325 A1 | 5/2012 | Allen et al. | | |
| 2012/0247466 A1 | 10/2012 | Avni | | |
| 2012/0285460 A1 | 11/2012 | Smith et al. | | |
| 2013/0112202 A1 * | 5/2013 | Fogelbrink | ......... | G06F 3/04847 128/204.21 |
| 2013/0133655 A1 | 5/2013 | Kimm et al. | | |
| 2013/0255689 A1 * | 10/2013 | Kim | .................... | A61M 16/201 128/205.24 |
| 2013/0263850 A1 | 10/2013 | Acker et al. | | |
| 2015/0174350 A1 * | 6/2015 | Ikei | .................... | A61M 16/0009 128/204.21 |
| 2015/0297306 A1 * | 10/2015 | Lazar | .................... | A61B 5/091 600/543 |
| 2015/0320951 A1 | 11/2015 | Acker et al. | | |
| 2016/0136367 A1 * | 5/2016 | Varney | .................. | A63B 23/18 128/202.13 |
| 2018/0133418 A1 * | 5/2018 | Brand | ............... | A61M 16/0006 |

FOREIGN PATENT DOCUMENTS

| | | |
|---|---|---|
| WO | 96/35468 A1 | 11/1996 |
| WO | 2010/058308 A2 | 5/2010 |

* cited by examiner

DEVICE FOR STIMULATING TRACHEOBRONCHIAL AIR

CROSS-REFERENCE TO RELATED APPLICATIONS

This application is a continuation of U.S. application Ser. No. 15/743,291 filed Jan. 10, 2018, which was a national stage application, filed under 35 U.S.C. § 371, of International Patent Application No. PCT/EP2016/066453 filed Jul. 11, 2016, which claims priority to FR Application No. 1556616 filed Jul. 10, 2015. Each of the previously noted applications is hereby incorporated by reference herein in their entirety.

FIELD OF INVENTION

The present invention pertains to the field of the treatment of obstructive ventilatory disorders. In particular, the invention relates to a device for stimulating mucus to improve its expectoration.

BACKGROUND OF INVENTION

In the healthy individual, the lungs are covered by a "film" called mucus, having a thickness of a few millimeters and a very fluid normal consistency. The function of this mucus is to protect the lung cells by isolating them from direct contact with air inspired by the lungs. The renewal of this mucus is ensured by cilia, mobile excrescences lying on the surface of the bronchi. These cilia, called vibratory cilia, beat towards the proximal part of the airways, eliminating the inhaled particles trapped in the gel phase of the mucus; said particles sliding on the layer of cilia, like on a conveyor belt. The clearance (the capacity of a mucociliary tissue, organ or organism to eliminate a substance from a given fluid) is carried out at a speed of 5 mm/min in the trachea, ensuring the renewal of the mucus layer every 20 minutes or so. This mucociliary clearance thus eliminates mucus to the pharynx where it will be swallowed or expectorated.

Now, there are various pathologies resulting in an obstructive ventilatory disorder, or pulmonary obstructive syndrome, which is characterized by a build-up of mucus and results in a limitation of flow rates in the respiratory tract and by an increase in air resistance.

More generally, this obstructive airway disorder is the result of a chronic condition corresponding to bronchiectasis (also called bronchiectasis or dilatation of the bronchi (DDB)), most often acquired as a result of a disease of the bronchi, lung or of the pleura. This bronchiectasis which may be localized or diffuse is characterized by dilatation of the small and medium-sized bronchi and is often accompanied by abundant muco-purulent sputum, which reflects the added infection.

The possible causes of bronchiectasis are multiple and include cystic fibrosis, COPD (eg, pulmonary emphysema or chronic bronchitis), especially severe early childhood infections (eg, bronchiolitis), ciliary dyskinesias (p. eg, KARTAGENER syndrome) or bronchial stenosis (by a foreign body or tumor), aftermath of pulmonary tuberculosis (the most common cause), or congenital or acquired Ig deficiency (A, G, or M).

Cystic fibrosis is a genetic disease affecting the glandular epithelia of many organs. It is the most common lethal genetic disease with autosomal recessive inheritance in Caucasian populations, while it is very rare in African and Asian populations. It is linked to mutations of the CFTR gene on chromosome 7, resulting in an alteration of the CFTR protein (Cystic Fibrosis Transmembrane Conductance Regulator), which is a chlorine-permeable ion channel whose function is to regulate the transport of chlorine through cell membranes. This alteration leads to an increase in mucus viscosity and its accumulation in the respiratory and digestive tracts. The disease affects many organs but respiratory disorders are predominant and account for most of the morbidity. The most common clinical form is associated with respiratory disorders, digestive disorders and staturoponderal growth disorders. There is no curative treatment but the progress of care has improved the quality and life expectancy of patients; in France, life expectancy at birth increased from 7 years in 1965 to 47 years in 2005.

The etiology of COPD or Chronic Obstructive Pulmonary Disease is very different from cystic fibrosis since its main cause is smoking. This disease is characterized by a slow and progressive obstruction of the airways and lungs, associated with permanent distention of the alveoli with destruction of the alveolar walls. COPD is mainly chronic bronchitis (eg bronchiolitis) or pulmonary emphysema, and the term of COPD appeared, because it is rare that a patient suffers from pure emphysema or pure chronic bronchitis. In the patient afflicted with COPD, the anaerobic metabolism is found preferentially required, to the detriment of aerobic metabolism. Maintenance and restoration of the function of aerobic metabolism appear today as major rehabilitation issues in favor of the quality of life of patients with COPD.

Another cause of bronchiectasis, primary ciliary dyskinesia (PCD) (also known as KARTAGENER or SIEWERT syndrome) is, like cystic fibrosis, a genetic disease affecting the respiratory system. The term dyskinesia describes the lack of ciliary movement observed because this disease affects the cilia of the body. Now, in addition to primary ciliary dyskinesia, and observed at birth, there is secondary ciliary dyskinesia (DCS), diagnosed later. PCD is not a contagious disease, but lung infections secondary to the disease can develop. Also, it is advisable to be careful in contact of PCD patients with sensitive patients (other PCD, MUCO, immunodepressed, . . . ). Now, for all these obstructive respiratory disorders, the patient shows an accumulation of bronchial mucus which, because of its stagnation, is responsible for infections that can lead to serious pulmonary complications. Also, is it important to perform a regular uncluttering in these patients.

For a long time, attempts have been made to use mucolytics or mucoregulators. Unfortunately, they have shown only a low medical service rendered and the treatments used today are therefore most often limited to the administration of bronchodilators and respiratory physiotherapy sessions. This treatment is in fact a "bronchial toilet", whose purpose is to avoid the superinfection that is most often the subject of these patients.

However, this bronchial toilet can be traumatic for the patient and remains of limited effectiveness when the mucus is too viscous or elastic.

Also, and in order to assist patients in this bronchial toilet, in the state of the art, various devices to facilitate the expulsion of mucus have been developed.

A device using IPV® (Intrapulmonary Percussive Ventilation) was invented in the 1980s by Dr. Forrest BIRD. This device involves the application of a breathing mask and the delivery of air to the patient in the form of powerful jerky pulsations of air so as to unhook the mucus of the bronchi and facilitate its expectoration by the patient. Such devices include the PERCUSIONATOR®. The use of this device is reported to be "traumatic", so this device is now rarely used.

Another device is described in patent FR 2,733,917, for stimulating the tracheobronchial air of a patient, by intra-pulmonary way, to fluidize the bronchial mucus. This document teaches that the inspired air must vibrate and that during the expiration, it is necessary to raise the cough of the patient by superimposing depressions of small amplitude and of short duration to avoid inducing the collapse of the bronchial walls. Indeed, FIG. 2 of the document shows that the amplitude of low depressions does not exceed 10 mbar and that the frequency of depressions is about 5 Hz, and according to the diagram, it can be observed about ten depressions per expiration and the duration of the expiration is about 2 seconds in the adult at rest, from which can be deduced the above-cited frequency. Thus, this document teaches on the one hand to cause coughing which generates an inconvenience in the patient and on the other hand that the pulses are of small amplitudes of the order of 10 mbar and low frequencies of the order of 5 Hz to avoid bronchial collapse. This document is considered the closest prior art.

Also there are known documents having the same drawback of generating depressions during inspiration and having the purpose of causing coughing.

Thus, the patent application US 2009/126734 teaches a device for stimulating the tracheobronchial air of a patient, by intra-pulmonary means, by using a source of pressurized gas delivering positive pressures using a valve for constituting percussive pulses of gas and two sensors, one measuring the pressure in the patient interface and the other measuring the pressure of the output line. Thus, said sensors provide a return on the pressure of the inspired and exhaled air to better determine the frequency of the impulses for the patient. A graphical interface makes it possible to display the operational parameters and to communicate with the controller managing the device and storing one or more therapeutic protocols making it possible to generate a first frequency during a first interval and then a second frequency.

U.S. Patent Application 2012285460 teaches a Mechanical Inspiration Expiration (MIE) apparatus having a fan, a steering valve, an oscillator, and a hose connector.

The fan is connected to the steering valve, which is connected to the oscillator, which is connected to the hose connector. During inspiration, a steering valve connects the exhaust of a positive pressure fan to an oscillator, and at the hose connector. During expiration, the steering valve connects the fan inlet to cause negative pressure at the hose connector and the oscillator. The oscillator is a butterfly valve with a 360° rotating disc. During inspiration, the disc modulates the airflow. During expiration, the oscillator is inactive or in the beat mode. When inactive, the disc is fixed to allow maximum airflow. In beat mode, the disk rotates continuously so that the airflow alternates rapidly between maximum and minimum flow. Finally, this document requires the user to press the expiration button during the expiration cycle (FIG. 10).

Application US 20050051174 teaches an improved inspiratory expiration pulse assisted system for bronchopulmonary secretions removal which includes a conduit for connection to the patient's airways, a source of pressure that provides through the conduit variations of pressure alternatively positive and negative at a first frequency corresponding to inspiration—expiration of the patient and a control mechanism allowing the pressure change during positive and negative pressure changes at a second higher frequency to periodically decrease the positive pressure during positive pressure variations and decreasing the negative pressure during negative pressure variations to provide percussion pulses during at least one inhalation-expiration to eliminate bronchopulmonary secretions from the patient's airways. Thus, this document teaches variations of pressure during inspiration and expiration of the patient.

From International patent application WO2010/058308 it is taught to create positive and negative pressure cycles during the inspirations and expirations of the patient.

All these devices generate pressure variations during inspiration and are intended to cause coughing.

Thus, these solutions have the disadvantage of causing expectoration, that is to say a cough, during the expiration of the patient. This implies a risk of collapse of the bronchial walls if the depression is not sufficiently small in amplitude and of short duration.

In this context, it is interesting to propose a solution that does not involve expectoration, that is to say that offers the patient the possibility of a passive expiration while improving the fluidification of the mucus. Indeed, the non-involvement of the respiratory muscles during expiration helps avoiding collapse.

SUMMARY

The object of the present invention is to overcome certain disadvantages of the prior art by proposing a device for stimulating tracheobronchial air of a patient suffering from an obstructive ventilatory disorder and able to modify the rheology of his tracheobronchial mucus, which includes:
(i) a negative pressure generator;
(ii) a physiological interface capable of interfacing the device with the patient's respiratory apparatus,
(iii) a connecting pipe connecting the physiological interface to the negative pressure generator, and characterized in that it further comprises
(iv) a control circuit capable of controlling said negative pressure generator, during the passive expiration phase, for the application of a succession of alternation of negative pressure and venting impulses with a determined frequency and a duty cycle determined during a first part of an expiration cycle and then a second frequency and a second duty cycle during a second part of the expiration cycle and to reiterate a defined number of expiration cycles.

According to another embodiment, the negative pressure generator comprises a vacuum pump with a flow rate greater than 20 L/min and a vacuum descent capacity of at least 200 mbar, a solenoid valve, a pneumatic base, a sound trap and a pressure sensor.

According to another embodiment, the control circuit comprises a pneumatic base, a solenoid valve and a pressure sensor.

According to another embodiment, the first part of an expiration cycle comprises a frequency of the order of 10 to 15 Hz and a duty cycle of 0.2 to 0.6 and the second part of an expiration cycle comprises a frequency of the order of 4 to 7 Hz and a duty cycle of the order of 0.4 to 0.8.

According to another embodiment, the first part of an expiration cycle comprises a frequency of 12 Hz and a duty cycle of 0.3 and the second part of an expiration cycle comprises a frequency of 6 Hz and a duty cycle of the order 0.6.

According to another embodiment, the control circuit is configured to adapt the expiration cycle previously chosen by the operator or the patient according to the results of evaluated average stimulation duration.

In another embodiment, the control circuit is configured to receive instructions from the operator or the patient to adjust the power of the first depressions according to their tolerance.

According to another embodiment, the physiological interface is equipped with an RFID tag for patient tracking.

According to another embodiment, the device further comprises a stopwatch for determining the duration of expirations during which the successive depressions are applied to the patient.

According to another embodiment, the device further comprises a calculator and a sensor making it possible, on the basis of the depression value and duration measured at each cycle, to determine the average value of depression and the average duration of stimulation applied during all cycles to the patient.

According to another embodiment, the device further comprises a communication module, in particular allowing the sending of an alert when the average duration of stimulation will mark a decrease of at least 20% for a patient and allows communication to a data control interface such as a touch pad.

According to another embodiment, the device further comprises a microcontroller card which, depending on the depression measured by the pressure sensor, is able to adapt the power applied to the negative pressure generator to obtain a desired value of depression applied to the tracheobronchial mucus of the patient.

In another embodiment, the microcontroller card is configured to adapt the power applied to the negative pressure generator to obtain a depression applied to the tracheobronchial mucus of the patient of between 40 and 100 millibars, preferably between 45 and 80 millibars, even more preferably between 50 and 100 millibars to the respiratory tract of the patient.

In another embodiment, the microcontroller card is configured to also control the power applied to the negative pressure generator as a function of the measured duration of stimulation.

According to another embodiment, the microcontroller card is configured to lower by 20% the power applied to the negative pressure generator as soon as the duration of stimulation goes below the critical threshold of 5 seconds during an expiration.

According to another embodiment, the microcontroller card makes it possible to increase by 10% the power applied to the negative pressure generator when the duration of stimulation exceeds the threshold of 9 seconds during an expiration.

According to another embodiment, the device comprises a dead man type security remote control.

BRIEF DESCRIPTION OF THE DRAWINGS

Other embodiments and advantages of the present invention will appear more clearly on reading the description below, made with reference to the accompanying drawings, in which.

DETAILED DESCRIPTION

The present invention relates to a device (1) for stimulating the tracheobronchial air of a patient (5) suffering from an obstructive ventilatory disorder and able to modify the rheology of his tracheobronchial mucus.

For the purposes of the present invention, the expression "obstructive ventilatory disorders" includes the pathologies listed above, but also extends to disorders associated with nasal obstruction, such as sinusitis, which corresponds to sinus obstruction following inflammation of the mucous membranes of the nose resulting in altered drainage of the nasal mucus.

Now, and preferably, the device according to the invention will target the bronchial mucus and will therefore aim at stimulating of intra-pulmonary air.

In some embodiments, the device includes a negative pressure generator (6) that includes a vacuum pump (7) with a flow rate greater than 20 L/min and a vacuum descent capacity of at least 200 mbar. Preferably, said vacuum pump (7) is a diaphragm pump. Preferably, said vacuum pump (7) has a flow rate greater than 40 L/min and a vacuum descent capacity of at least 300 mbar. In some embodiments, said vacuum pump (7) is connected on its suction outlet to a control circuit via a splined tip (71) and said vacuum pump (7) is connected to its blower outlet to a sound trap (8). Said sound trap (8) is a padded cylinder system which has the advantage of attenuating the sound produced during the passage of air in the system.

In some embodiments, the device comprises a physiological interface (2) capable of interfacing the device with the patient's respiratory apparatus (5). This physiological interface (2) preferably comprises a mouthpiece or a breathing mask. Preferably, said physiological interface is equipped with an RFID tag (20) for tracking the patient.

In some embodiments, the device comprises a connecting pipe (4) connecting the physiological interface (2) to a pneumatic base (3) through the outlet (35) of said base (3), said connecting pipe (4) being preferably flexible.

The passive expiration performed with the device of the present invention can provide an expiratory aid, which will increase expiratory time. The expiration is ensured by the machine, thus passive for the patient, which avoids the physiological bronchial collapse which is a major obstacle to the uncluttering of the airways. This prolonged expiration allows reaching the peripheral airways, which are usually the main "target" of the uncluttering maneuvers.

In certain embodiments, the device comprises a control circuit, capable by a particular arrangement, of controlling, during the passive expiration phase, the application of a succession of alternation of negative pressure and venting with a determined frequency, defining a cycle, and at least one determined duty cycle. Preferably, these parameters are applied during a first part of an expiration cycle, then a second frequency and a second duty cycle are applied during a second part of the expiration cycle, by repeating a defined number of expiration cycles. Said control circuit preferably comprises a pneumatic base (3) which contains a vacuum chamber (31), preferably at least 40 ml. Said pneumatic base (3) preferably comprises a pressure sensor (32) which is connected, via a tube, to an orifice (33) of the pneumatic base (3). In addition, said pressure sensor (32) advantageously takes the form of a relative pressure sensor measuring the value of the vacuum with respect to the ambient atmospheric pressure. On this type of sensor, pressure fluctuations due to weather or altitude changes have a direct impact on the measured value. If the pressure exerted on the relative pressure sensor is lower than the ambient pressure, it is called negative relative pressure or, more generally, depression, and the value is preceded by a sign "−".

Relative pressure sensors have a well-known structure and typically only have one pressure connection. The ambient pressure is exerted through a slot or a vent tube located at the rear of the sensor membrane and this relative measurement is compensated for. The invention being in closed circuit, and in depression, a single sensor is sufficient for the device. The Applicant has been able to demonstrate that it was important to optimize the efficacy of the treatment and avoid the variability between patients, that the depression be maintained within a specific interval within an expiration cycle. This specific time interval is referred to herein as the "duty cycle" and defines the ratio between the time during which depression is applied to the patient and the total duration of a cycle. In other words, this duty cycle corresponds to the time during which the patient's lungs are subjected to depression. The control of this time makes it possible in particular to avoid that it is too long and presents a risk of causing the collapse of the bronchi. In addition, this modulation of the duty cycle of each depression makes it possible, beyond the depression generated which has a shearing action on the bronchial mucus and which therefore causes its viscosity to drop, to apply a flow that is longer or shorter, which improves the secretions transport. More specifically, it is important that the depression applied to the tracheobronchial mucus be between 40 and 100 millibars, preferably between 45 and 80 millibars, and preferably between 50 and 100 millibars. Said control circuit also preferably comprises a solenoid valve (9) which preferably has an opening diameter of less than 6 mm and an opening time of greater than 20 ms. Said solenoid valve (9) is connected to said pneumatic base (3) via a screw pitch (34).

Said control circuit has the advantage of being able to vary the fluidification power of the device via a microcontroller card (10) which controls the switching frequency of the solenoid valve (9) and the opening and closing times of the solenoid valve (9). Preferably, the first part of an expiration cycle comprises a frequency of the order of 10 to 15 Hz and a duty cycle of 0.2 to 0.4 and the second part of a cycle comprises a frequency of order of 4 to 7 Hz and a duty cycle of the order of 0.5 to 0.8. Preferably, the first part of an expiration cycle comprises a frequency of 12 Hz and a duty cycle of 0.3 and the second part of a cycle comprises a frequency of 6 Hz and a duty cycle of the order of 0.6. Preferably, the defined number of expiration cycles is initially selected by the operator or patient (5) and is adapted by the apparatus according to the results of the evaluated average stimulation duration.

Figure 1:
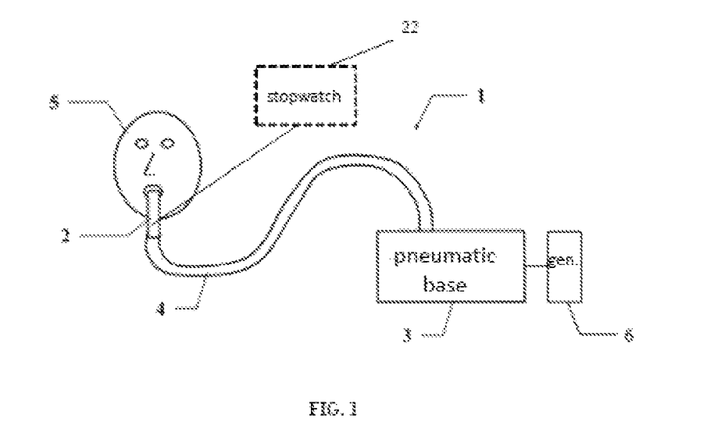
FIG. 1 represents the device connected to the patient.
Figure 2:
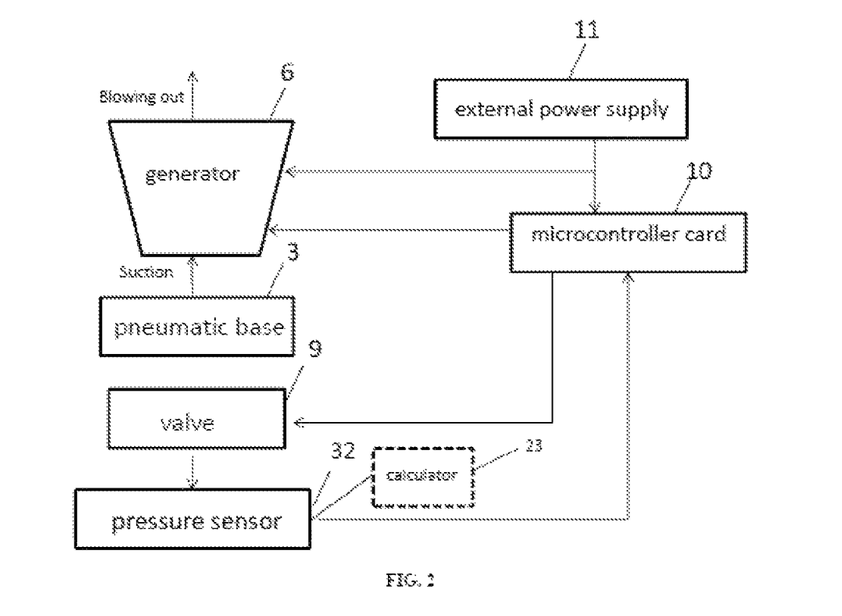
FIG. 2 represents a diagram of the operation of the device.
Figure 3:
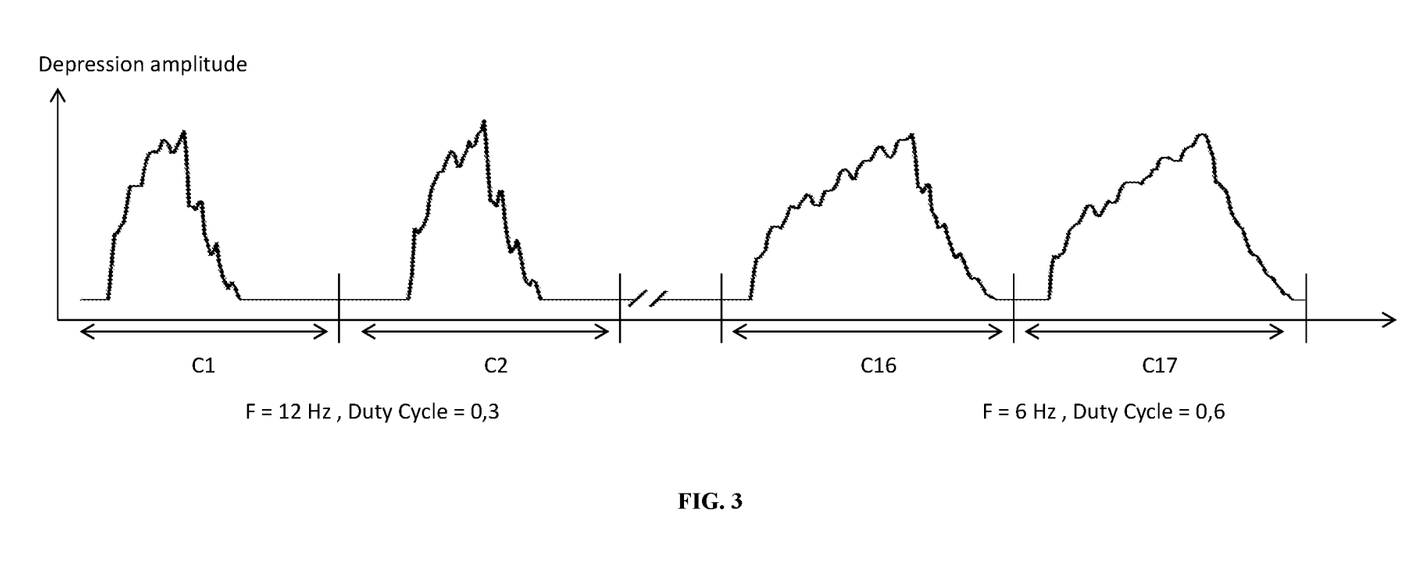
FIG. 3 represents an example of the depression signals generated by the device.
Figure 4:
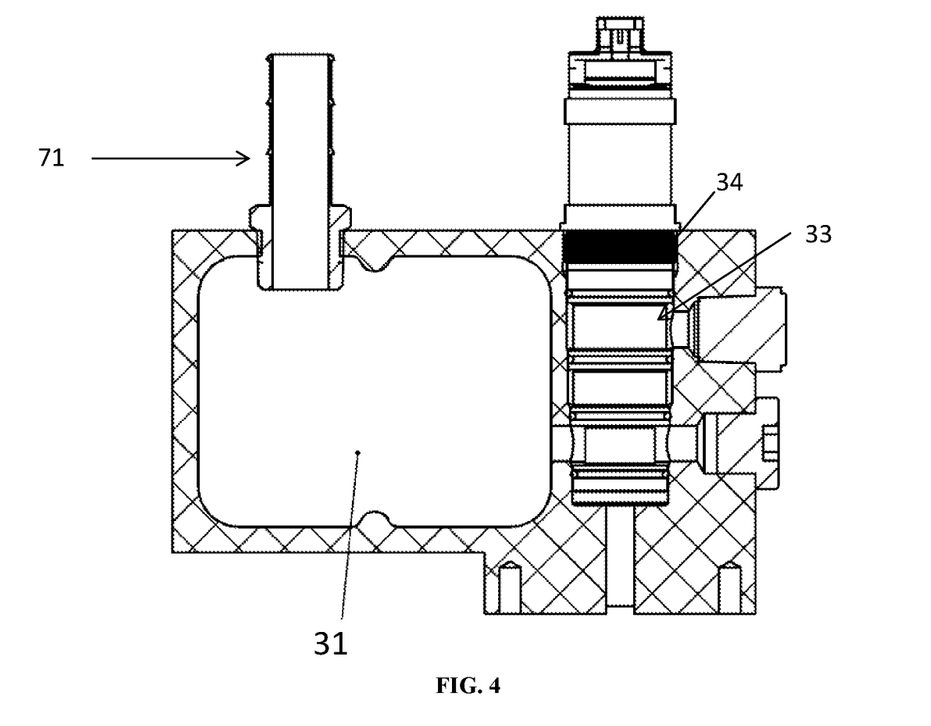
FIG. 4 represents a sectional view of the base.
Figure 5:
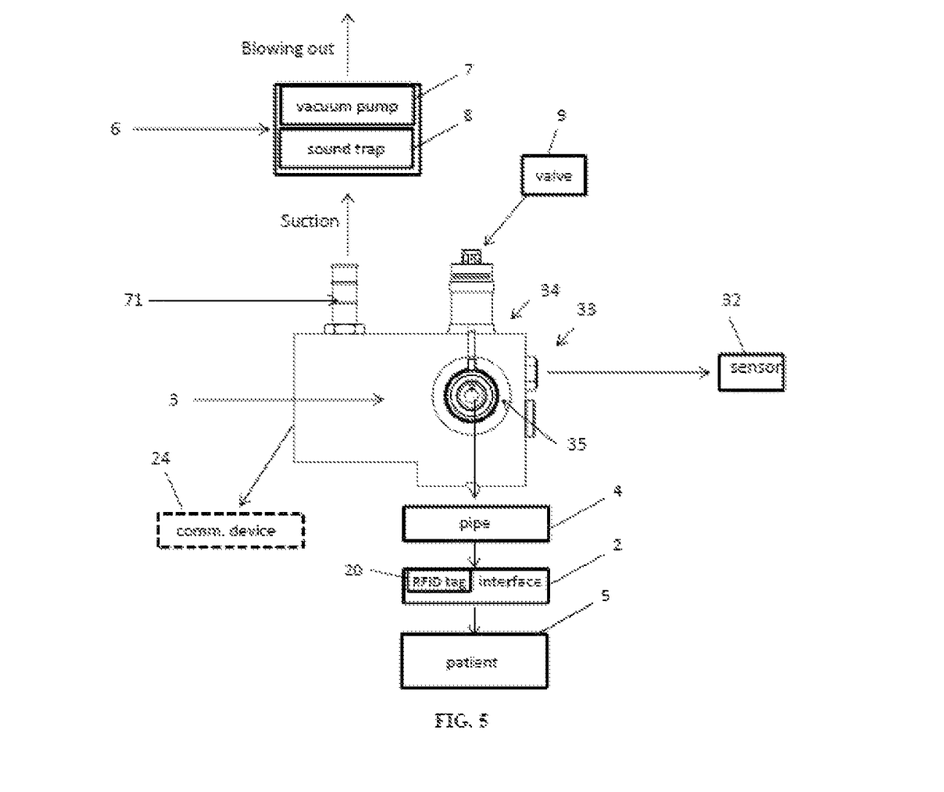
FIG. 5 shows an overall view of the system, with the face base.

For example, in an illustrative and non-limiting manner according to FIG. 3 (C1 and C2), for a duty cycle of 30%, the negative pressure generator (6) will empty the vacuum chamber (31) for 70% of ¹⁄₁₂th of a second, and the patient (5) will be connected to this vacuum chamber (31) for 30% of ¹⁄₁₂th of a second. The period of about 83 ms of such a frequency of 12 Hz is therefore decomposed for the patient in a suction period (depression) of about 24 ms and a pause period of about 58 ms. This causes a brief and strong depression and therefore a stronger fluidification power by thixotropy.

For example, in an illustrative and non-limiting manner according to FIG. 3 (C16 and C17), for a duty cycle of 60%, the negative pressure generator (6) will empty the vacuum chamber (31) for 40% of ⅙th of a second, and the patient (5) will be connected to this vacuum chamber (31) for 60% of ⅙th of a second. The period of about 166 ms of such a frequency of 6 Hz is therefore decomposed for the patient in a suction period (depression) of about 100 ms and a pause period of about 66 ms. This causes a weaker and longer depression, therefore a lower fluidification power but a greater drainage capacity by transmitting the kinetic energy between the air and the mucus over a longer time, that is to say 60% of a cycle.

To be noted that in FIG. 3, the time is cut between a first part and a second part of the treatment, but especially that the time scale represented for the first two cycles (C1 C2) illustrated is about twice as fast as that of the two subsequent cycles (C16, C17) illustrated, since these last appear only about two times slower than these first, whereas they are about four times slower. On the other hand, as shown for example, in an illustrative and non-limiting manner according to FIG. 3, a session can be carried out as follows: firstly, 15 passive expiration cycles at 12 Hz with a duty cycle of 30%, one thus obtains a strong fluidification power by thixotropy, then one carries out 15 cycles of passive expiration at 6 Hz with a cyclic ratio of 70%, one thus obtains a drainage by transmission of the kinetic energy. During inspirations, the patient (5) disconnects from the device and inhales normally.

In some embodiments, the device further includes a stopwatch (22) for determining the duration of each depression applied to the patient (5). The stopwatch (22) has the advantage of assisting the expiration of the patient (5). Thus, for an expiratory cycle to be effective, it is important for the stimulation to take place for a minimum period of at least five seconds and therefore for the expiration of patient (5) to be maintained for at least this period. Indeed, a short time of stimulation of the patient (5) during expiratory phases materializes a low respiratory capacity and a descent into depression too fast. This results in too much power of the suction device that empties too quickly the patient's lung volume (5).

In some embodiments, the device further includes a calculator (23) that, based on the depression value and duration thereof measured at each cycle, determines the average applied vacuum value and the average stimulation duration during all cycles to the patient (5). Thus, said calculator (23) stores in its memory each command of the solenoid valve (9), each value of the signal from the sensor and representative of the amplitude or power of the vacuum measured instantaneously and the number of control cycles of the solenoid valve (9) for the entire duration (determined by a scalable parameter stored by the apparatus) of the expiration cycle to allow the calculator (23) by a calculation using the power values and the cycle number to determine the average depression value measured at each cycle, then memorized and then determined the average depression value applied during all the cycles performed by the patient (5) during the treatment session. The calculator (23) associated with the sensor also measures during the time intervals when the solenoid valve (9) is closed, so as not to apply a depression impulse, the evolution of the pressure in the lung of the patient (5) during the expiration and the time required to reach the pressure value corresponding to an expiration and stored as a threshold in the device. This time corresponding to the duration of an expiration cycle is stored and used by the device. This value representative of the duration of the expiration cycle will be compared with a first threshold value, stored by the calculator (23) which represents a value of minimum duration for the calculator (23) to adjust the power of depression generated by the device when the representative value of the duration of an expiration cycle drops below the minimum value set. A second threshold value which represents a maximum duration of the expiration cycle and stored by the calculator (23) is used by the latter in comparison with the measured duration to generate a control signal of the increase of the depression if the duration of the cycle measured exceeds the second saved value.

In some embodiments, the device further comprises a communication module (24), in particular allowing the sending of an alert when the average stimulation duration will mark a decrease of at least 20% for a patient (5). Thus, the communication module (24) is able to establish a wireless communication with at least one remote device according to a given distinct communication protocol. In this way, said communication module (24) makes it possible to transmit data to referent health professionals, in particular the average or instantaneous depression value, the average or instantaneous stimulation duration or in agreement with any change in the treatment, especially any decrease marked of one or the other thus constituting a revealer which could indicate a deterioration of the patient's condition (5). In one embodiment, a measurement signal processing algorithm is used for comparing the latter to a determined threshold established 20% below the set value provided by the programming system and sending an alert when the average stimulation time will be at least 20% less for a patient (5). Indeed, such a sudden drop is a sign of a decrease in the respiratory and muscular capacity of the patient (5).

In some embodiments, the device further includes a microcontroller card (10) which, depending on the depression measured by the pressure sensor (32), and the user-determined parameters within a range defined by a set of desirable parameters stored in the memory associated with the microcontroller card (10), will be able to adapt the power applied to the negative pressure generator (6) to obtain a desired value of depression applied to the tracheobronchial mucus of the patient (5). Preferably, the microcontroller card (10) will adapt the power applied to the negative pressure generator (6) to obtain a depression applied to the tracheobronchial mucus of the patient (5) of between 40 and 100 millibars, preferably between 45 and 100 millibars, more preferably between 45 and 80 millibars, preferably between 50 and 100 millibars. In this way, the treatment applied to the patient (5) by the device will achieve optimal efficiency and limit the impact of interpatient variability. Similarly, the microcontroller card (10) can also control the power applied to the negative pressure generator (6) as a function of the measured pacing time. The microcontroller operating program monitors the stimulation duration and compares it to a critical threshold, to decrease by a percentage the power applied to the negative pressure generator (6). Thus, in the case where the stimulation duration goes below the critical threshold of 5 seconds, the microcontroller card (10) can lower by 20% the signal representative of the power setpoint applied to the negative pressure generator (6), and therefore the depression applied to the lung volume. This decrease makes it possible to lower the rate at which the pulmonary volume is emptied and thus to increase the tolerance of the patient (5). In the case, however, where the stimulation time exceeds the high threshold of 9 seconds, the microcontroller card (10) can increase by 10% the power applied to the negative pressure generator (6), and thus the depression applied to the lung volume. This increase makes it possible to adjust the fluidification performance induced by the power of the depression.

In some embodiments, the device includes a dead man type security remote control, which must be actively actuated continuously or regularly reset by the patient (5), during the treatment, for the device to operate. Otherwise, the device stops.

Preferably, an external power supply (11) supplies the various components of the device according to the invention that are the negative pressure generator (6), the pressure sensor (32), the stopwatch and the microcontroller card (10). Following the startup of the device according to the invention, the microcontroller card (10) will adjust the power of the negative pressure generator (6) so as to obtain the selected value of depression (mbar).

The following detailed description will be better understood when read in conjunction with the drawings. For the purpose of illustrating, the device is shown in the preferred embodiments. It should be understood, however that the application is not limited to the precise arrangements, structures, features, embodiments, and aspect shown. The drawings are not drawn to scale and are not intended to limit the scope of the claims to the embodiments depicted. Accordingly, it should be understood that where features mentioned in the appended claims are followed by reference signs, such signs are included solely for the purpose of enhancing the intelligibility of the claims and are in no way limiting on the scope of the claims.

While various embodiments have been described and illustrated, the detailed description is not to be construed as being limited hereto. Various modifications can be made to the embodiments by those skilled in the art without departing from the true spirit and scope of the disclosure as defined by the claims.

The invention claimed is:

1. A device for stimulating tracheobronchial air of a patient suffering from an obstructive ventilatory disorder and able to modify a rheology of tracheobronchial mucus of the patient, the device comprising:
   a negative pressure generator;
   a physiological interface configured to interface the device with a respiratory system of the patient;
   a connecting pipe connecting the physiological interface to the negative pressure generator;
   a control circuit configured to control said negative pressure generator, the control circuit generating a passive phase by applying a succession of alternations of negative pressure and venting impulses with a first determined frequency and a first determined duty cycle during a first part of an expiration cycle, and then with a second determined frequency and a second determined duty cycle during a second part of said expiration cycle, a duty cycle corresponding to a ratio between the duration during which the negative pressure is applied and the total duration of said expiration cycle, the control circuit being configured to reiterate a defined number of expiration cycles,
   wherein the first part of the expiration cycle comprises the first determined frequency of the order of 10 to 15 Hz and the first determined duty cycle of 0.2 to 0.7, and the second part of the expiration cycle comprises the second determined frequency of the order of 4 to 7 Hz and the second determined duty cycle of the order of 0.5 to 0.8.

2. The device according to claim 1, wherein the negative pressure generator comprises
   a vacuum pump with a flow rate greater than 20 L/min and a vacuum descent capacity of at least 200 mbars, and
   a sound trap.

3. The device according to claim 1, wherein the control circuit comprises
   a pneumatic base, a solenoid valve, and
   a pressure sensor.

4. The device according to claim 3, further comprising a microcontroller card configured to adapt a power applied to the negative pressure generator to obtain a desired value of respective alternations of negative pressure and venting impulses applied to the tracheobronchial mucus of the patient depending on a respective one of the alternations of negative pressure and venting impulses measured by the pressure sensor.

5. The device according to claim 4, wherein the microcontroller card is configured to adapt the power applied to the negative pressure generator to obtain a respective one of the alternations of negative pressure and venting impulses applied to the tracheobronchial mucus of the patient of between 40 and 100 millibars to the respiratory tract of the patient.

6. The device according to claim 5, wherein the respective one of the alternations of negative pressure and venting impulses applied to the tracheobronchial mucus of the patient is between 45 and 80 millibars to the respiratory tract of the patient.

7. The device according to claim 5, wherein the respective one of the alternations of negative pressure and venting impulses applied to the tracheobronchial mucus of the patient is between 50 and 100 millibars to the respiratory tract of the patient.

8. The device according to claim 4, wherein the microcontroller card is configured to control the power applied to the negative pressure generator as a function of a measured duration of stimulation.

9. The device according to claim 8, wherein the microcontroller card is configured to lower the power applied to the negative pressure generator by 20% as soon as the measured duration of stimulation goes below a critical threshold of 5 seconds during an expiration.

10. The device according to claim 8, wherein the microcontroller card is configured to increase the power applied to the negative pressure generator by 10% when the measured duration of stimulation exceeds a threshold of 9 seconds during an expiration.

11. The device according to claim 1, wherein the first part of said expiration cycle comprises the first determined frequency of 12 Hz and the first determined duty cycle of the order of 0.3, and the second part of said expiration cycle comprises the second determined frequency of 6 Hz and the second determined duty cycle of the order of 0.6.

12. The device according to claim 1, wherein the control circuit is configured to adapt the expiration cycle previously chosen by an operator or the patient according to results of an evaluated average stimulation duration.

13. The device according to claim 1, wherein the control circuit is configured to receive instructions from an operator or the patient to adjust a power of the alternations of negative pressure and venting impulses.

14. The device according to claim 1, wherein the physiological interface is equipped with a radio frequency identification (RFID) tag for patient tracking.

15. The device according to claim 1, further comprising a stopwatch configured to determine a duration of expirations during which the successive alternations of negative pressure and venting impulses are applied to the patient.

16. The device according to claim 1, further comprising a calculator configured to determine, based on a depression value and a duration thereof measured at each expiration cycle, an average value of the respective alternations of negative pressure and venting impulses and an average duration of stimulation applied during all expiration cycles to the patient.

17. The device according to claim 1, further comprising a communication module configured to send an alert when an average duration of stimulation marks a decrease of at least 20% for a patient, the communication module being configured to communicate with a data control interface.

18. The device according to claim 17, wherein the data control interface is a touch pad.

19. The device according to claim 1, further comprising a dead man security remote control.

* * * * *